(12) United States Patent
Lyons et al.

(10) Patent No.: US 6,707,049 B1
(45) Date of Patent: Mar. 16, 2004

(54) IRRADIATION SYSTEM WITH COMPACT SHIELD

(75) Inventors: Stan V. Lyons, Brentwood, CA (US); Steven E. Koenck, Cedar Rapids, IA (US); Brian T. Dalziel, Marion, IA (US); Douglas C. White, Cedar Rapids, IA (US); Janette J. Kewley, Marion, IA (US)

(73) Assignee: Mitec Incorporated, Cedar Rapids, IA (US)

( * ) Notice: Subject to any disclaimer, the term of this patent is extended or adjusted under 35 U.S.C. 154(b) by 231 days.

(21) Appl. No.: 09/814,472

(22) Filed: Mar. 21, 2001

Related U.S. Application Data

(60) Provisional application No. 60/191,028, filed on Mar. 21, 2000.

(51) Int. Cl.[7] .......................... G01N 21/00; G01N 23/00
(52) U.S. Cl. ................ 250/453.11; 422/22; 250/455.11
(58) Field of Search ..................... 250/492.2, 492.3, 250/455.11, 453.11

(56) References Cited

U.S. PATENT DOCUMENTS

| | | |
|---|---|---|
| 924,284 A | 6/1909 | Smith |
| 1,809,078 A | 6/1931 | Smith |
| 2,095,502 A | 10/1937 | Johnston .................. 21/54 |
| 2,456,909 A | 12/1948 | Brasch .................... 21/54 |
| 2,602,751 A | 7/1952 | Robinson .................. 99/221 |
| 2,741,704 A | 4/1956 | Trump et al. ............. 250/49.5 |
| 2,816,231 A | 12/1957 | Nygard .................... 250/43 |
| 2,824,969 A | 2/1958 | Crowley-Milling ........ 250/49.5 |
| 2,963,369 A | 12/1960 | Urbain .................... 99/107 |
| 2,989,735 A | 6/1961 | Gumpertz ................ 340/174.1 |
| 3,087,598 A | 4/1963 | Clore ..................... 198/38 |
| 3,224,562 A | 12/1965 | Bailey et al. ............. 198/131 |
| 3,261,140 A | 7/1966 | Long et al. ............... 53/22 |
| 3,396,273 A | 8/1968 | Brunner .................. 250/52 |
| 3,452,195 A | 6/1969 | Brunner .................. 250/52 |
| 3,560,745 A | 2/1971 | Petersen et al. ........... 250/83 |
| 3,564,241 A | 2/1971 | Ludwig ................... 250/52 |
| 3,567,462 A | 3/1971 | Silverman et al. ......... 99/157 |
| 3,676,673 A | 7/1972 | Coleman ................. 250/49.5 |
| 3,676,675 A | 7/1972 | Ransohoff et al. ......... 250/52 |
| 3,876,373 A | 4/1975 | Glyptis ................... 21/54 |
| 3,974,391 A | 8/1976 | Offermann ............... 250/492 |
| 4,013,261 A | 3/1977 | Steigerwald et al. ....... 250/453 |
| 4,066,907 A | 1/1978 | Tetzlaff .................. 250/453 |
| 4,151,419 A | 4/1979 | Morris et al. ............. 250/453 |
| 4,201,920 A | 5/1980 | Tronc et al. ............. 250/492 |
| 4,281,251 A | 7/1981 | Thompson et al. ........ 250/398 |
| 4,484,341 A | 11/1984 | Luniewski ................ 378/69 |
| 4,652,763 A | 3/1987 | Nablo .................... 250/492.3 |
| 4,663,532 A | 5/1987 | Roche .................... 250/400 |
| 4,757,201 A | 7/1988 | Kanter ................... 250/337 |
| 4,760,264 A | 7/1988 | Barrett ................... 250/453.1 |
| 4,767,930 A | 8/1988 | Stieber et al. ............ 250/396 |

(List continued on next page.)

Primary Examiner—John R. Lee
Assistant Examiner—Johnnie L Smith, II
(74) Attorney, Agent, or Firm—Kinney & Lange, P.A.

(57) ABSTRACT

An irradiation system includes a radiation source providing radiation in a localized radiation exposure area and a shielding structure around the radiation source. A conveyance system transports product into the shielding structure, through the radiation exposure region and out of the shielding structure. The conveyance system includes an input portion for carrying the product into the shielding structure at a first elevation. A first elevator moves the product from the first elevation to a second elevation different from the first elevation. A processing portion of the conveyance system carries the product at the second elevation through the radiation exposure region. A second elevator moves the product from the second elevation to a third elevation different from the second elevation. An output portion of the conveyance system carries the product out of the shielding structure at the third elevation.

23 Claims, 8 Drawing Sheets

U.S. PATENT DOCUMENTS

| | | | |
|---|---|---|---|
| 4,785,178 A | 11/1988 | Lynch et al. | 250/496.1 |
| 4,788,701 A | 11/1988 | Barrett | 378/69 |
| 4,852,138 A | 7/1989 | Bergeret et al. | 378/69 |
| 4,864,595 A | 9/1989 | Barrett | 378/69 |
| 4,866,281 A | 9/1989 | Bosshard | 250/453.1 |
| 4,870,368 A | 9/1989 | Putnam | 328/233 |
| 4,908,221 A | 3/1990 | Barrett | 426/240 |
| 4,974,503 A | 12/1990 | Koch | 99/451 |
| 5,004,926 A | 4/1991 | Vassenaix et al. | 250/492.3 |
| 5,008,550 A | 4/1991 | Barrett | 250/453.1 |
| 5,026,983 A | 6/1991 | Meyn | 250/233 R |
| 5,096,553 A | 3/1992 | Ross et al. | 204/157.15 |
| 5,101,168 A | 3/1992 | Miller | 328/233 |
| 5,323,442 A | 6/1994 | Golovanivsky et al. | 378/119 |
| 5,362,442 A | 11/1994 | Kent | 422/22 |
| 5,366,746 A | 11/1994 | Mendenhall | 426/521 |
| 5,396,071 A | 3/1995 | Atwell et al. | 250/358.1 |
| 5,396,074 A | 3/1995 | Peck et al. | 250/453.11 |
| 5,400,382 A | 3/1995 | Welt et al. | 378/69 |
| 5,434,421 A | 7/1995 | Burth | 250/434 |
| 5,451,790 A | 9/1995 | Enge | 250/436 |
| 5,461,656 A | 10/1995 | Golovanivsky et al. | 378/66 |
| 5,470,597 A | 11/1995 | Mendenhall | 426/521 |
| 5,482,726 A | 1/1996 | Robinson, Jr. | 426/238 |
| 5,530,255 A | 6/1996 | Lyons et al. | 250/492.3 |
| 5,554,856 A | 9/1996 | Bidnyy et al. | 250/455 |
| 5,557,109 A | 9/1996 | Bidnyy et al. | 250/455 |
| 5,590,602 A | 1/1997 | Peck et al. | 104/88.01 |
| 5,593,713 A | 1/1997 | De La Luz-Martinez et al. | 426/237 |
| 5,597,597 A | 1/1997 | Newman | 426/248 |
| 5,603,972 A | 2/1997 | McFarland | 426/240 |
| 5,635,714 A | 6/1997 | Nablo et al. | 250/305 |
| 5,661,305 A | 8/1997 | Lawrence et al. | 250/397 |
| 5,690,978 A | 11/1997 | Yin et al. | 426/237 |
| 5,801,387 A | 9/1998 | Nablo et al. | 250/492.3 |
| 5,834,744 A | 11/1998 | Risman | 219/697 |
| 5,838,760 A | 11/1998 | Moses | 378/119 |
| 5,847,401 A | 12/1998 | McKeown et al. | 250/396 |
| 5,881,534 A | 3/1999 | Ahlqvist et al. | 53/403 |
| 5,994,706 A | 11/1999 | Allen et al. | 250/454.11 |
| 6,023,497 A | 2/2000 | Takahashi et al. | 378/57 |
| 6,027,754 A | 2/2000 | Bushnell et al. | 426/238 |
| 6,051,185 A * | 4/2000 | Beers | 422/22 |
| 6,066,348 A | 5/2000 | Yuan et al. | 426/236 |
| 6,086,932 A | 7/2000 | Gupta | 426/237 |
| 6,096,379 A | 8/2000 | Eckhoff | 427/428 |
| 6,127,687 A | 10/2000 | Williams et al. | 250/492.3 |
| 6,429,444 B1 | 8/2002 | Korenev et al. | 250/492.3 |

* cited by examiner

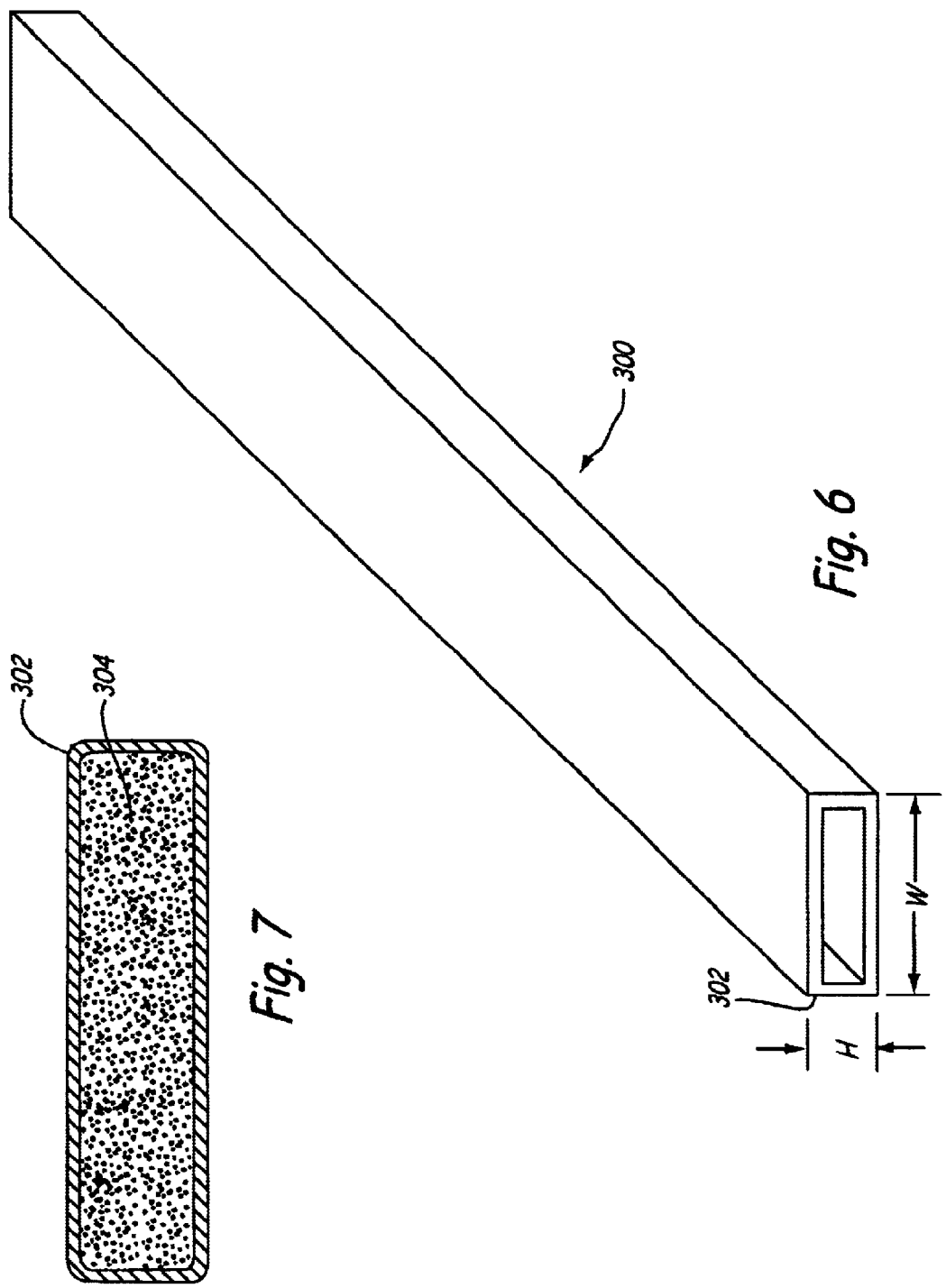

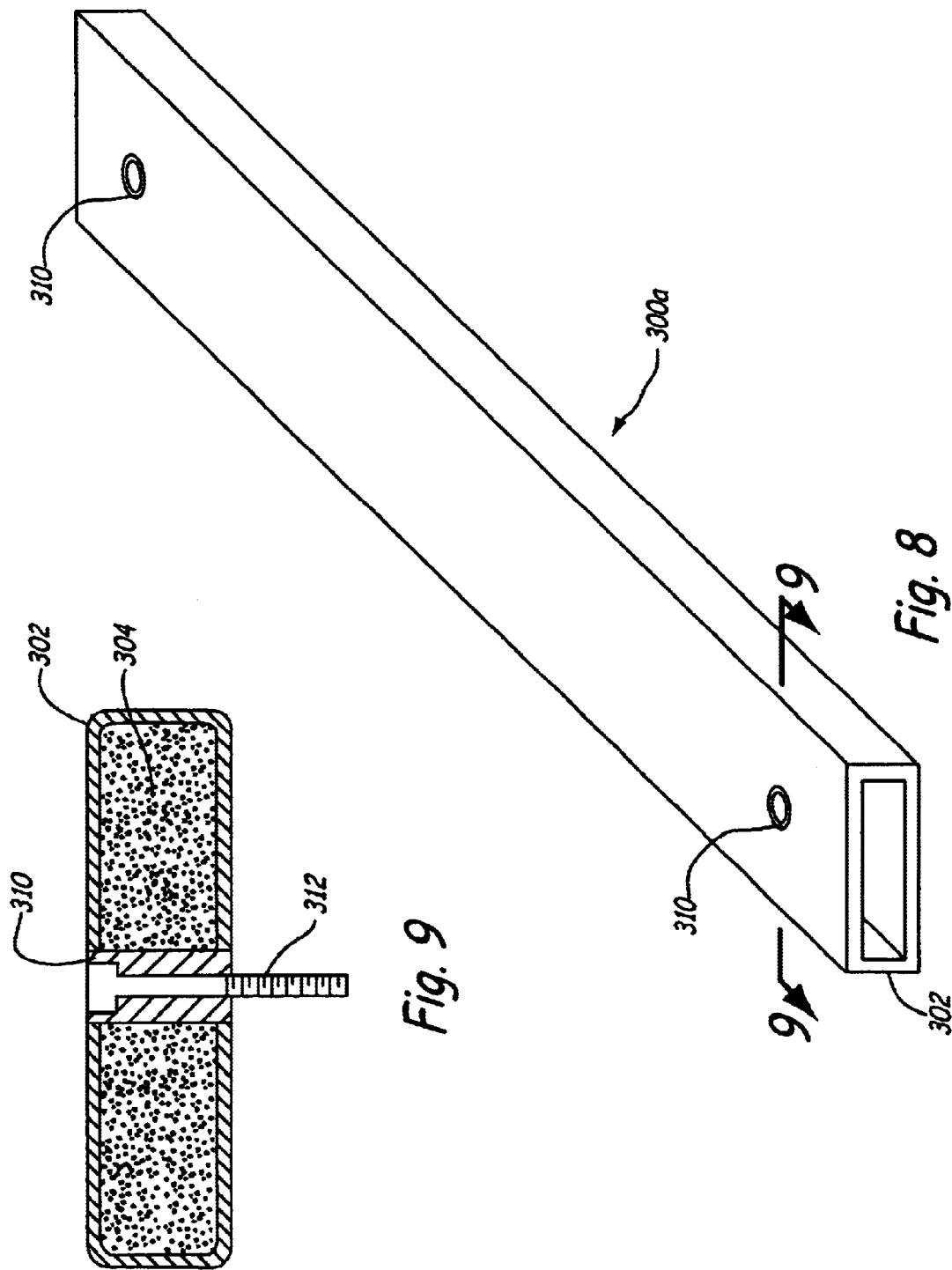

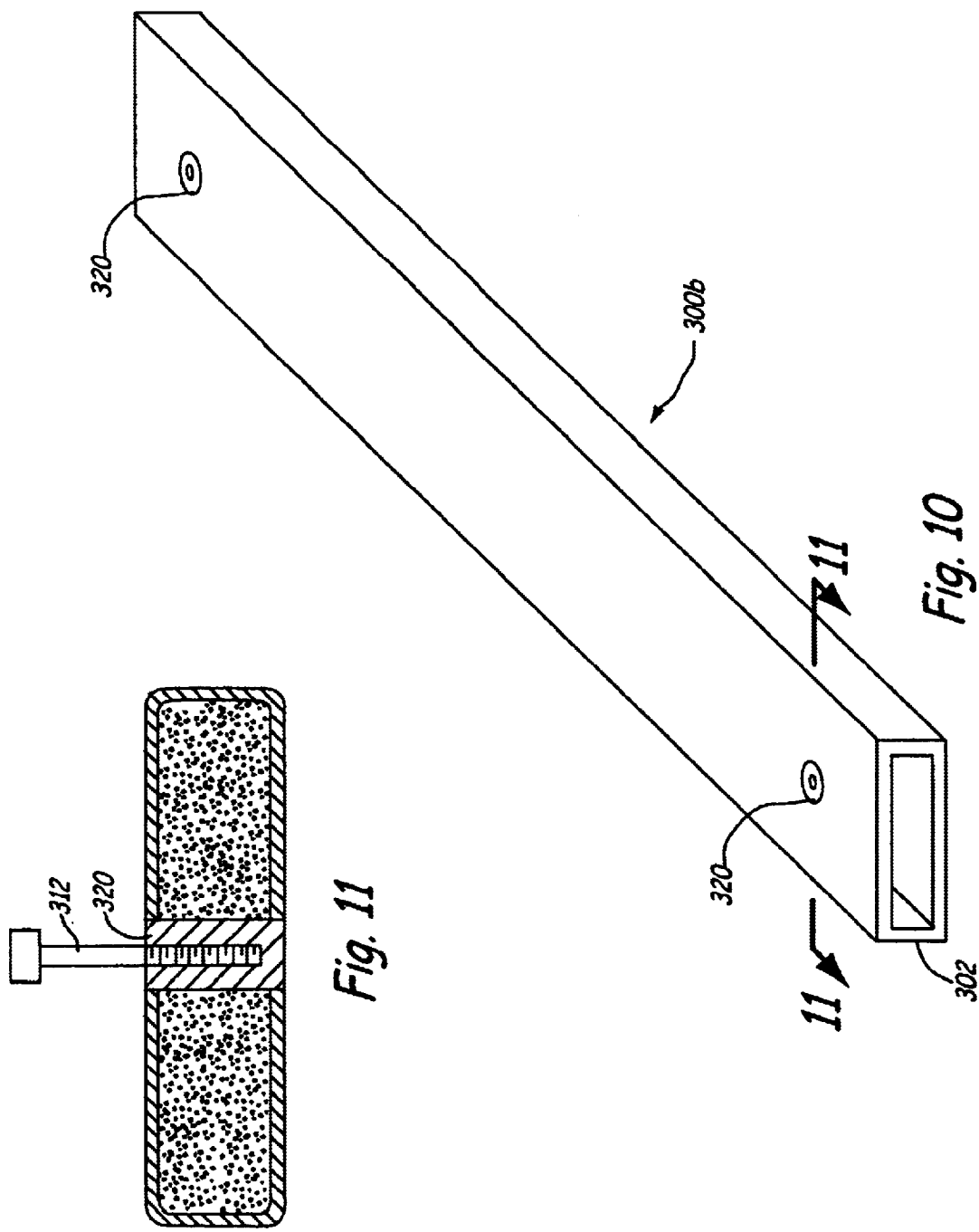

IRRADIATION SYSTEM WITH COMPACT SHIELD

CROSS-REFERENCE TO RELATED APPLICATION(S)

This application claims the benefit of Provisional Application No. 60/191,028 filed Mar. 21, 2000 for "Irradiation System With Compact Shield" by S. Lyons, S. Koenck, B. Daiziel, D. White and J. Kewley.

INCORPORATION BY REFERENCE

The aforementioned Provisional Application No. 60/191,028 is hereby incorporated by reference in its entirety.

BACKGROUND OF THE INVENTION

The present invention relates to an irradiation system, and more particularly to a system having a compact shield arrangement for containing radiation within the system to ensure the safety of operating personnel.

Irradiation technology for medical and food sterilization has been scientifically understood for many years dating back to the 1940's. The increasing concern for food safety as well as safe, effective medical sterilization has resulted in growing interest and recently expanded government regulatory approval of irradiation technology for these applications. The available sources of ionizing radiation for irradiation processing consist primarily of gamma sources, high energy electrons and x-ray radiation. The most common gamma source for irradiation purposes is radioactive cobalt 60 which is simple and effective but expensive and hazardous to handle, transport, store and use. For these reasons, electron beam and x-ray generation are becoming the preferred technologies for material irradiation. An exemplary maximum electron beam energy for irradiation purposes is on the order of 10 million electron-volts (MeV) which results in effective irradiation without causing surrounding materials to become radioactive. The necessary electron beam power must be on the order of 5 to 10 kilowatts or more to effectively expose materials at rates sufficient for industrial processing.

Electron beam and x-ray irradiation systems both employ an electron accelerator to either emit high velocity electrons directly for irradiation or to cause high velocity electrons to collide with a metal conversion plate which results in the emission of x-rays. A number of electron acceleration techniques have been developed over the past several decades including electrostatic acceleration, pumped cylindrical accelerators and linear accelerators.

Electrostatic accelerators are characterized by the use of a direct current static voltage of typically 30 to 90 kilovolts which accelerates electrons due to charge attraction. Electrostatic accelerators are limited in maximum energy by the physical ability to generate and manage high static voltage at high power levels. Electrostatic accelerators using Cockroft-Walton voltage multipliers are capable of energy levels of up to 1 MeV at high power levels, but the 10 MeV energy level utilized by many systems for effective irradiation is not typically available.

Various types of pumped cylindrical electron beam accelerators have been known and used for many years. These accelerators generally operate by injecting electrons into a cylindrical cavity, where they are accelerated by radio frequency energy pumped into the cylinder. Once the electrons reach a desired energy level, they are directed out of the cylinder toward a target.

RF linear accelerators have also generally been in use for many years and employ a series of cascaded microwave radio frequency tuned cavities. An electron source with direct current electrostatic acceleration injects electrons into the first of the cascaded tuned cavities. A very high energy radio frequency signal driven into the tuned cavities causes the electrons to be pulled into each tuned cavity by electromagnetic field attraction and boosted in velocity toward the exit of each tuned cavity. A series of such cascaded tuned cavities results in successive acceleration of electrons to velocities up to the 10 MeV level. The accelerated electrons are passed through a set of large electromagnets that shape and direct the beam of electrons toward the target to be irradiated.

A typical industrial irradiation system employs an electron beam accelerator of one of the types described, a subsystem to shape and direct the electron beam toward the target and a conveyor system to move the material to be irradiated through the beam. The actual beam size and shape may vary, but a typical beam form is an elliptical shape having a height of approximately 30 millimeters (mm) and a width of approximately 45 mm. The beam is magnetically deflected vertically by application of an appropriate current in the scan deflection electromagnets to cause the beam to traverse a selected vertical region. As material to be irradiated is moved by conveyor through the beam, the entire volume of product is exposed to the beam. The power of the beam, the rate at which the beam is scanned and the rate that the conveyor moves the product through the beam determines the irradiation dosage. Electron beam irradiation at the 10 MeV power level is typically effective for processing of food materials up to about 3.5 inches in thickness with two-sided exposure. Conversion of the electron beam to x-ray irradiation is relatively inefficient but is effective for materials up to 18 inches or more with two-sided exposure.

In electron beam irradiation, high energy electrons are directed toward various food products which cause secondary radiation to be generated to penetrate deeply within the product. A byproduct of this beneficial secondary radiation is the generation of potentially harmful scattered radiation in the area of the system while it is operating. Consequently, radiation shielding is necessary to insure the safety of operating personnel.

Shielding requirements are determined by the power and the energy of the radiation source. Energy is related to the velocity of the accelerated electrons and generally determines penetration capability. Power is related to the number of accelerated electrons and generally determines exposure rate capability. For personnel safety, both parameters must be considered, as each contributes to the ability of radiation to penetrate shielding structures in amounts that must be limited for safe long term exposure by humans.

Electron beam irradiation systems maybe designed at various power and energy levels, with the maximum allowable energy established by the FDA and USDA at 10 MeV. This level has been selected as an upper bound due to the fact that no materials are activated and rendered radioactive by exposures at or below this level. While useful irradiation processing may be performed with electron beam energies as low as 1 MeV, the penetration depth that is possible at such energies is well less than 0.3 inches and is therefore limited in application. Energies of 10 MeV, however, allow two sided penetration up to 3.5 inches, which is useful for a wide variety of food products in final packaging. The disadvantage of the higher irradiation energy sources is the fact that shielding requirements are substantially greater to insure the safety of operating personnel. Typical 10 MeV systems are constructed within entire special buildings constructed of continuously poured high density concrete that may be as thick as 10 feet. Materials are typically moved to the radiation source by a conveyor that moves around a maze structure in circuitous fashion to insure that there is no straight line path for radiation to escape. While such structures are effective in providing safe operating conditions, they are also expensive and inefficient to construct and operate, and are difficult to add to an existing facility or production system.

There is a need in the art for an irradiation system employing a compact and yet effective shielding system for containing irradiation and preserving the safety of operating personnel. Such a system is the subject of the present invention.

BRIEF SUMMARY OF THE INVENTION

The present invention is an irradiation system that includes a radiation source providing radiation in a localized radiation exposure area and a shielding structure around the radiation source. A conveyance system transports product into the shielding structure, through the radiation exposure area and out of the shielding structure. The conveyance system includes an input portion for carrying the product into the shielding structure at a first elevation. A first elevator moves the product from the first elevation to a second elevation different from the first elevation. A processing portion of the conveyance system carries the product at the second elevation through the radiation exposure area. A second elevator moves the product from the second elevation to a third elevation different from the second elevation. An output portion of the conveyance system carries the product out of the shielding structure at the third elevation. This configuration allows the shielding structure to have a reduced size in comparison to prior art irradiation systems, so that the irradiation system may be more easily added to existing processing facilities, or simply installed in a smaller area. The compact shielding structure may also be built for less cost than the concrete bunker required by many prior art irradiation systems.

In another embodiment, the conveyance system includes first and second input portions for carrying the product into the shielding structure and first and second output portions for carrying the product out of the shielding structure. A first elevator moves the product from the first input portion at first elevation to a second elevation different from the first elevation, and a second elevator moves the product from the second input portion at the first elevation to the second elevation. A first transfer portion of the conveyance system controllably transfers the product from the first and second elevators to a processing portion of the conveyance system for carrying the product through a localized radiation exposure area, and on to a second transfer portion of the conveyance system for controllably passing the product. A third elevator moves the product passed from the second transfer portion at the second elevation to the first output portion of the conveyance system at a third elevation different from the second elevation, and a fourth elevator moves the product passed from the second transfer portion at the second elevation to the second output portion of the conveyance system at the third elevation. This embodiment potentially increases the throughput of the irradiation system, and provides a redundant product path to reduce down time in the case of failure of one of the input portions or output portions of the conveyance system.

BRIEF DESCRIPTION OF THE DRAWINGS

FIG. 6 is a perspective diagram of a shield component piece according to an embodiment of the present invention.

FIG. 7 is a section view of the shield component piece shown in FIG. 6.

FIG. 8 is a perspective diagram of a shield component piece including an attachment mechanism according to an embodiment of the present invention.

FIG. 9 is a section view of the shield component piece shown in FIG. 8.

FIG. 10 is a perspective diagram of a shield component piece including a receiving chamber for an attachment mechanism according to an embodiment of the present invention.

FIG. 11 is a section view of the shield component piece shown in FIG. 10.

DETAILED DESCRIPTION

Figure 1:
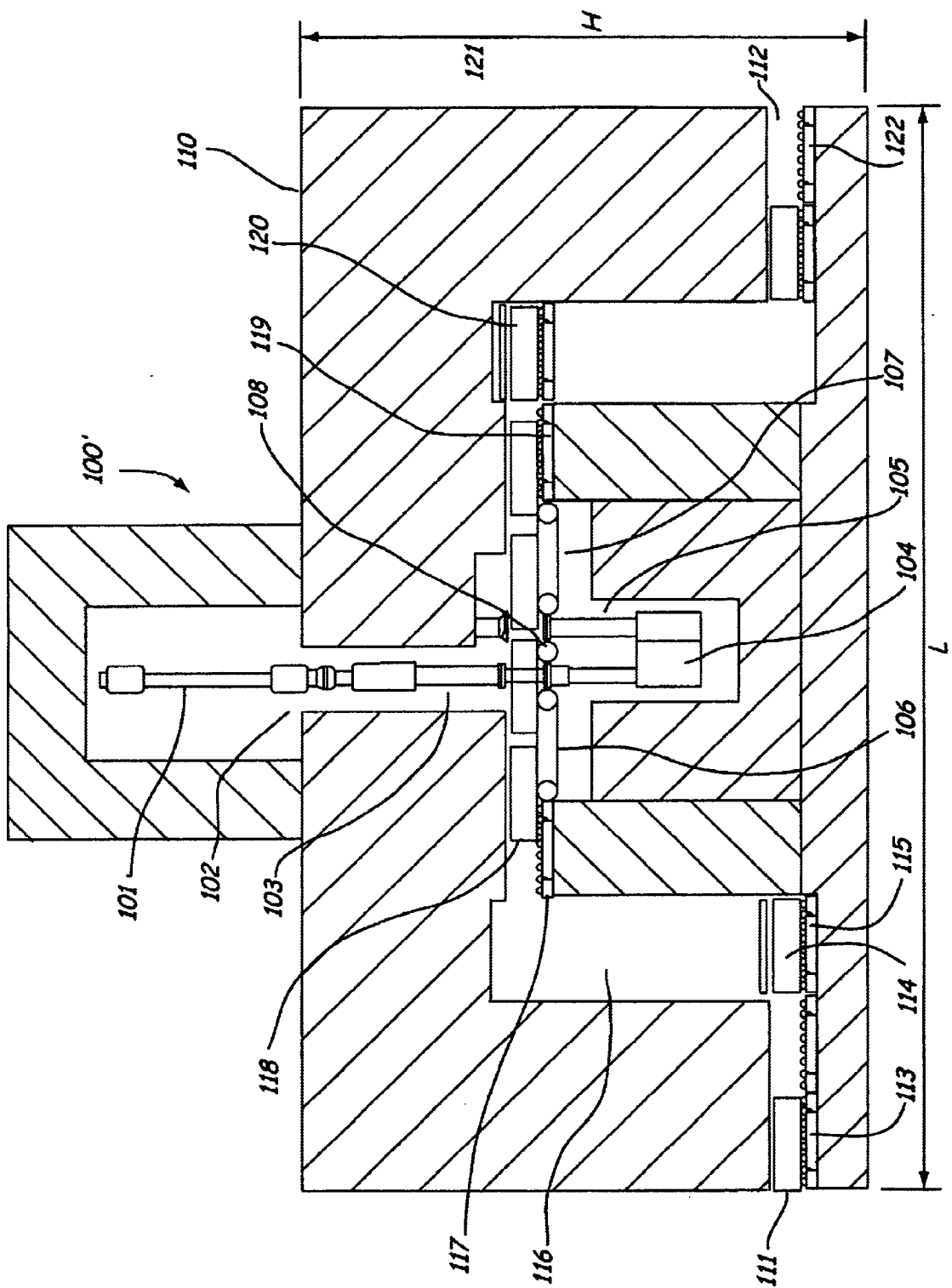
FIG. 1 is a side section view of an irradiation system employing a compact shielding module and an elevator assembly according to a first embodiment of the present invention.

FIG. 1 is a side section view of irradiation system 100 employing a compact shielding module and an elevator assembly according to a first embodiment of the present invention. Irradiation system 100 employs electron beam accelerator 101 with energy as high as 10 MeV, and does not require a special concrete bunker structure to provide the necessary safety shielding for operating personnel. Irradiation system 100 is shown in FIG. 1 with a two sided exposure structure using single accelerator 101, but a single sided exposure system could use the described shielding system equally effectively. Accelerator 101 accelerates electrons to an energy of up to 10 MeV and directs the electrons through output aperture 102 downward to upper scan horn 103, and through bending magnet 104 to lower scan horn 105. The two sided exposure system uses electromagnets in a manner generally known in the art to alternately deflect electrons either toward upper scan horn 103 (to direct the electrons by a second electromagnet toward the top of the material to be irradiated) or past upper scan horn 103 to bending magnet 104 that directs the beam back upward through additional electromagnets into lower scan horn 105 (to direct electrons toward the bottom of the material to be irradiated). Material to be irradiated is typically packaged in boxes that are moved at constant and controlled speed past the localized radiation area defined by upper and lower scan horns by conveyors 106 and 107. Center roller 108 moves at the same speed as conveyors 106 and 107 to support product boxes as they move from the infeed conveyor 106 to the outfeed conveyor 107. While the general concept of a conveyor system is known in the art of irradiation systems, irradiation system 100 of the present invention employs a novel compact self-shielded structure 110 that completely surrounds the high energy radiation-producing portions of the system. Shielding structure 110 is composed of radiation absorbing material such as steel, concrete, lead or a combination of those materials, placed closely around entrance 111 and exit 112 of irradiation system 100. A box of material to be irradiated is inserted at entrance 111 by being placed on powered entrance rollers or conveyor 113 which moves the box toward position 114. Elevator carrier 115 with powered rollers is positioned in elevator shaft 116 to elevate the box to a level even with infeed buffer rollers 117. When elevator carrier 115 reaches the same level as infeed buffer rollers 117, it is stopped and the rollers of elevator carrier 115 and infeed buffer rollers 117 move the box off elevator carrier 115 and into a position to be moved to infeed conveyor 106. When elevator carrier 115 is empty, it returns to the lower position to receive another box from entrance rollers 113.

Box 118 that has been placed on infeed buffer rollers 117 is moved onto infeed conveyor 106 at a speed generally faster than the speed of infeed conveyor 106 and outfeed conveyor 107 as soon as it is determined by position sensors located near infeed conveyor 106 that there is a space available and the previous box being irradiated will not be bumped by the new one being loaded.

A similar process is used to move boxes from outfeed conveyor 107 onto outfeed buffer rollers 119. These rollers may also generally move at a speed faster than infeed conveyor 106 and outfeed conveyor 107 and are timed with the position of output elevator carrier 121 to insure that the elevator is located in its upper position to receive a box at position 120. When the box is loaded at position 120, output elevator carrier 121 is moved to the lower position to place the box even with exit rollers 122 and out exit 112 of irradiation system 100. When output elevator carrier 121 is empty, it returns to the upper position to receive another box from outfeed buffer rollers 119.

The movement of boxes from entrance rollers 113 through irradiation system 100 may be controlled by a Programmable Logic Controller (PLC) of typical industrial type. Sensors may be placed at various locations through the material flow process to monitor the movement and insure that operation is occurring as desired. The goal of the material handling system is to move boxes into the system, up the elevator and onto infeed conveyor 106 at a rate that keeps boxes positioned as close as possible to each other without touching to maximize the throughput of irradiation system 100 without upsetting the precise irradiation exposure ensured by the constant speed of the material moving through the localized radiation exposure area defined by scan horns 103 and 105.

In an exemplary embodiment, the overall size of the described system is on the order of 24 feet long, 11 feet wide and 17 feed tall. The actual shielding thickness may vary from the illustration depending on the locations of the highest intensity of scattered radiation. The generally rectangular shape and conveyor material movement is compatible with production conveyor systems and is compact enough to be place inside typical processing and material handling facilities. Boxes containing materials of density similar to water such as meat up to 3.5 inches thick may be irradiated effectively. The total height of the boxes in the present example may be up to 6 inches thick, however, dimensions may be modified to increase or decrease sizes for particular applications.

Figure 2:
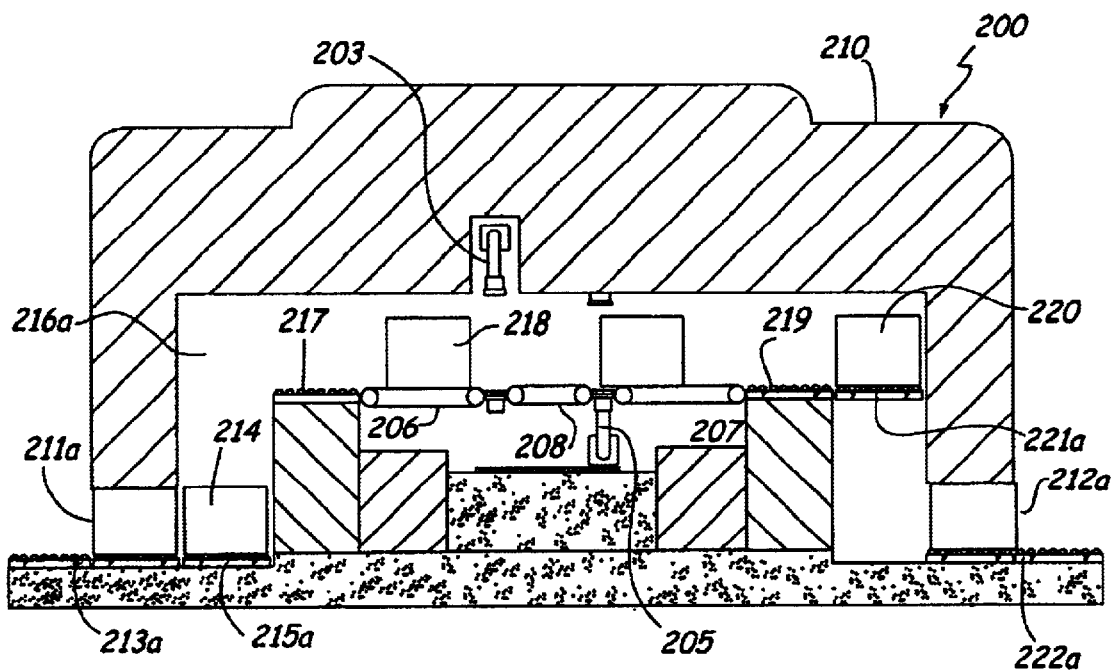
FIG. 2 is a side section view of an irradiation system employing a compact shielding module and dual path elevator assemblies according to a second embodiment of the present invention.

FIG. 2 is a side section view of irradiation system 200 employing a compact shielding module and dual elevator assemblies according to a second embodiment of the present invention. Irradiation system 200 includes at least one accelerator (not shown in FIG. 2 for purposes of clarity) for accelerating electrons to an energy as high as 10 MeV, and directs the electrons through scan horns 203 and 205 shown schematically in FIG. 2. The two sided exposure system may be realized in the manner described above with respect to FIG. 1, or may employ dual accelerators, for example. For purposes of illustration, irradiation system 200 will be described and shown as utilizing dual accelerators.

Product boxes to be irradiated are moved at constant and controlled speed past a localized radiation area (defined by upper scan horn 203 and lower scan horn 205) by conveyors 206 and 207. Center roller 208 moves at the same speed as conveyors 206 and 207 to support product boxes as they move from infeed conveyor 206 to outfeed conveyor 207. Shielding structure 210 completely surrounds the high energy radiation-producing portions of irradiation system 200. Shielding structure 210 is composed of radiation absorbing material such as steel, concrete, lead or a combination of those materials, placed closely around entrances 211a and 211b (FIG. 3) and exits 212a and 212b (FIG. 3) of irradiation system 200.

Figure 3:
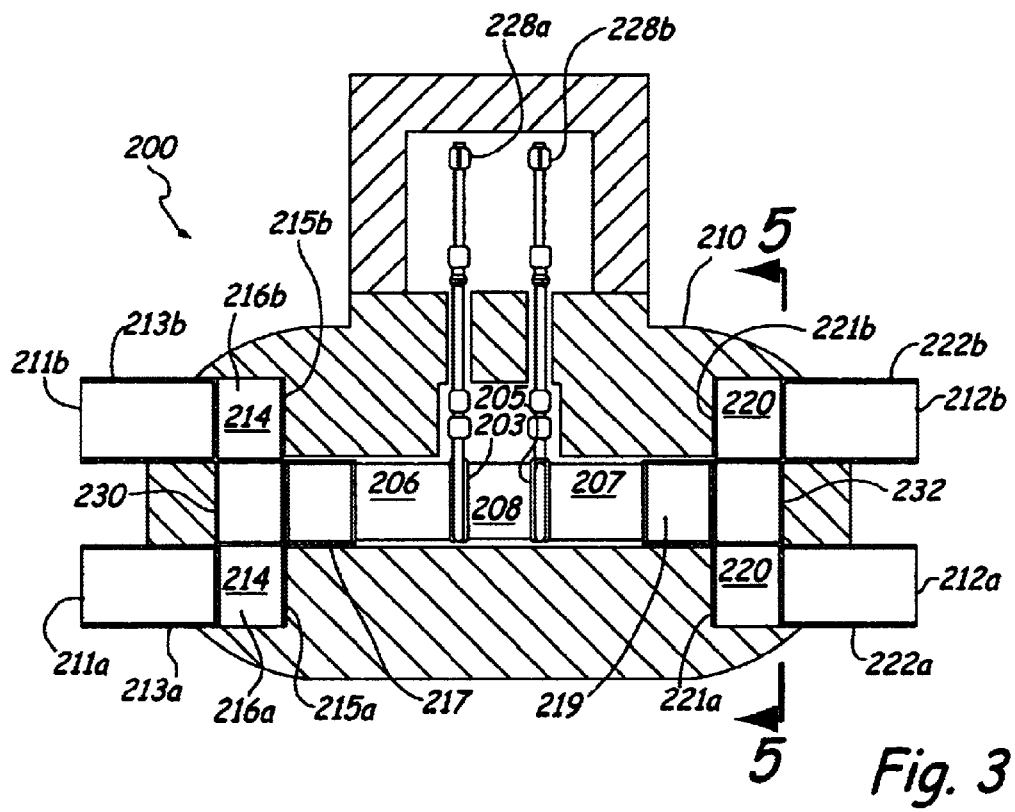
FIG. 3 is a top section view of the irradiation system shown in FIG. 2.

FIG. 3 is a top section view of irradiation system 200 shown in FIG. 2, illustrating the dual path elevator configuration of the system. Accelerators 228a and 228b are provided within shield structure 210 to direct accelerated electrons through scan horns 203 and 205, respectively. Boxes of material to be irradiated are inserted at entrances 211a and 211b by being placed on powered entrance rollers or conveyors 213a and 213b, which moves the boxes toward position 214 on elevator carriers 215a and 215b. Elevator carriers 215a and 215b with powered rollers are positioned in elevator shafts 216a and 216b, respectively, to elevate the boxes to a level even with transfer area rollers 230. The system is controlled so that a product box is moved from a selected one of elevator carriers 215a and 215b to transfer area rollers 230 when the selected elevator carrier reached the same level as transfer area rollers 230, and the selected elevator carrier is stopped at that level. Transfer area rollers 230 move the product box positioned thereon to infeed buffer rollers 217 and into a position to be moved to infeed conveyor 206. When the selected one of elevator carriers 215a and 215b is empty, it returns to the lower position to receive another box from the appropriate one of entrance rollers 213a and 213b.

Box 218 (FIG. 2) that has been placed on infeed buffer rollers 217 is moved onto infeed conveyor 206 at a speed generally faster than the speed of infeed conveyor 206 and outfeed conveyor 207 as soon as it is determined by position sensors located near infeed conveyor 206 that there is a space available and the previous box being irradiated will not be bumped by the new one being loaded.

A similar process is used to move boxes from outfeed conveyor 207 onto outfeed buffer rollers 219. These rollers may also move at a speed faster than infeed conveyor 206 and outfeed conveyor 207, and are operable to move product boxes to transfer area rollers 232. Transfer area rollers 232 are timed with the position of output elevator carriers 221a and 221b to insure that one of the elevators is located in its upper position to receive a box at position 220. When the box is loaded at position 220, the selected one of output elevator carriers 221a and 221b is moved to the lower position to place the box even with the appropriate one of exit rollers 222a and 222b, and out the corresponding one of exits 212a and 212b. When the selected elevator carrier is empty, it returns to the upper position to receive another box from transfer area rollers 232.

Similar to the single path system described above with respect to FIG. 1, dual path elevator irradiation system 200 may be controlled by a PLC of typical industrial type, with sensors placed at various locations through the material flow process to monitor the movement and insure that operation is occurring as desired. The goal of the material handling system is to move boxes into the system, up the elevators and onto infeed conveyor 206 at a rate that keeps boxes positioned as close as possible to each other without touching to maximize the throughput of irradiation system 200 without upsetting the precise irradiation exposed ensured by the constant speed of the material moving through the localized radiation exposure area defined by scan horns 203 and 205. By utilizing dual input and output material movement paths and dual input and output elevators, the throughput of irradiation system 200 may be increased in some embodiments in comparison to the single path system, since the potentially limiting speed of the elevators in moving between their lower positions and upper positions is effectively doubled by employing two elevators in parallel. In addition, should one of the elevators employed in irradiation system 200 fail, the system can still operate with a single elevator (albeit at potentially reduced throughput), protecting against the possibility of a full shutdown which would be quite problematic for the typically time-sensitive applications of food irradiation, for example.

Figure 4:
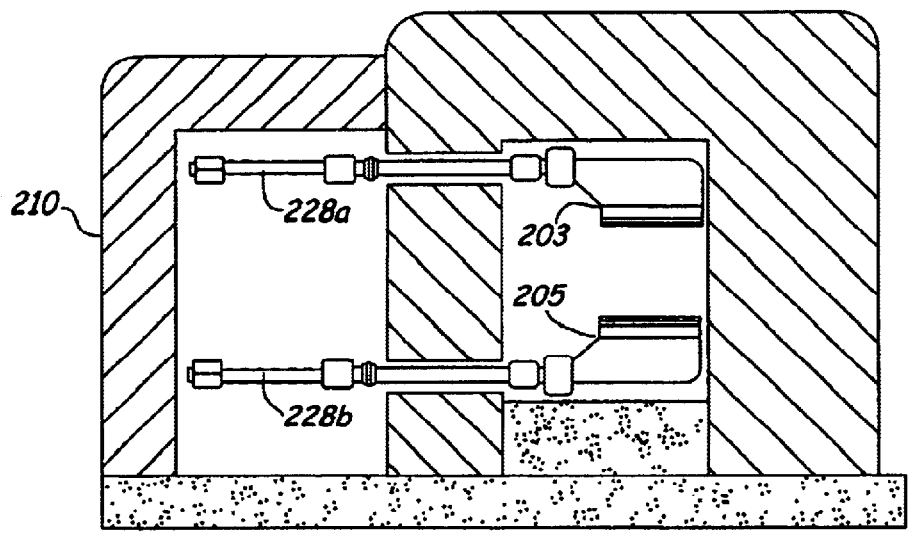
FIG. 4 is a schematic cross-sectional view through the center of the irradiation system shown in FIG. 2.

FIG. 4 is a schematic cross-sectional view through the center of irradiation system 200 shown in FIG. 2, illustrating dual accelerators 228a and 228b within shielding module 210 in more detail. Accelerators 228a and 228b are operable to accelerate electrons to energies up to 10 MeV and direct the accelerated electrons through scan horns 203 and 205 onto material to be irradiated. Alternatively, a single accelerator could be used with appropriate electromagnets for deflecting the beam through an upper and lower path, as generally described above with respect to FIG. 1.

Figure 5:
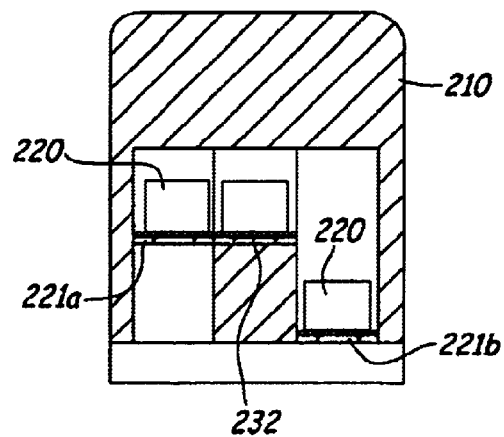
FIG. 5 is a section view taken at line 5—5 of FIG. 3.

FIG. 5 is a section view taken at line 5—5 of FIG. 3, illustrating the configuration of output elevator carriers 221a and 221b and transfer area rollers 232 in more detail. Elevator carriers 221a and 221b are operated in an exemplary embodiment to alternately move between an upper position for receiving a box from transfer area rollers 232 (as shown by elevator carrier 221a) and a lower position for moving a box through the exit of the irradiation system (as shown by elevator carrier 221b).

Although the present invention has been described with respect to machine-generated irradiation, it should be understood that alternate embodiments of the invention may employ other sources of radiation that are known in the art. These alternate sources of radiation are generally not directable by electromagnets as described above with respect to machine-generated electron beams, but may be configured to expose product to radiation in a localized radiation area having a similar arrangement to the devices shown in FIGS. 1–5.

The elevator configuration employed by the present invention, in conjunction with the shielding structure around the irradiation system, is effective to insure that radiation is contained within the shielding structure and is unable to escape into areas where operating personnel may be present. As illustrated in FIGS. 1 and 2, shielding structures 110 and 210 are configured in such a manner that there is no line-of-sight path for radiation to escape from the irradiation processing area to the exits of the irradiation system, due to the 90 degree turn and change in elevation provided by the elevators employed by the system. Moreover, by utilizing elevators to provide 90 degree turns in the material movement path, the overall footprint of the self-shielded irradiation system can be made much smaller than prior art irradiation systems, with a floor area of 264 square feet in an exemplary embodiment of irradiation system 100 shown in FIG. 1, and a floor area of 494 square feet in an exemplary embodiment of irradiation system 200 shown in FIGS. 2–5.

FIG. 6 is a perspective diagram, and FIG. 7 is a section view, of shield structural component 300 according to an exemplary embodiment of the present invention. Structural component 300 has a roughly tubular shape, with outer material layer 302 defining an inner chamber to be filled with shielding material 304. In an exemplary embodiment, outer material layer 302 is composed of a strong structural material such as steel or stainless steel, and shielding material 304 is composed of a radiation attenuating material such as lead. An exemplary height H of structural component 300 is about 2 inches, and an exemplary width W of structural component 300 is about 8 inches. A shield (such as shield 110 (FIG. 1) or shield 210 (FIG. 2)) can be constructed with a plurality of structural components 300 stacked and interconnected with one another. In an exemplary embodiment, each structural component 300 has an intrinsic strength sufficient to support its own weight and the weight of an adjacent structural component (in the event that the adjacent structural component should structurally fail). Structural components 300 may optionally be constructed with sufficient strength to support the weight of more than one adjacent structural component, for additional safety against structural failure.

FIG. 8 is a perspective diagram, and FIG. 9 is a section view taken along line 9—9 of FIG. 8, illustrating structural component 300a designed to interconnect with other structural components to form a radiation shield according to an embodiment of the present invention. Structural component 300a includes outer material layer 302 with shielding material 304 in the inner chamber defined thereby, and also includes apertures 310 extending at least partially through outer material layer 302 and shielding material 304. As shown in FIG. 9, in an exemplary embodiment apertures 310 are solid cylindrical plugs that include a drilled hole and a countersink for receiving fasteners 312. Fasteners 312 may be of a type known in the art, such as a threaded bolt in an exemplary embodiment, for connection to adjacent structural components.

FIG. 10 is a perspective diagram, and FIG. 11 is a section view taken along line 11—11 of FIG. 10, illustrating structural component 300b designed to interconnect with structural component 300a (FIG. 8) to form a radiation shield according to an embodiment of the present invention. Structural component 300b includes outer material layer 302 with shielding material 304 in the inner chamber defined thereby, and also includes threaded apertures 320 extending at least partially through outer material layer 302 and shielding material 304. As shown in FIG. 1, in an exemplary embodiment apertures 320 are solid cylindrical plugs that include a threaded hole for receiving fasteners 312. Fasteners 312 may be of a type known in the art, such as a threaded bolt in an exemplary embodiment, for connection to adjacent structural component 300a (FIG. 8).

In an exemplary embodiment, structural components 300 are liquid-tight in construction, so that shielding material 304 can be installed by pouring molten material such as lead into the chamber defined by outer material layer 302 through an access port. In one embodiment, molten shielding material is poured into structural components 300 after the solid cylindrical plugs have been inserted in apertures 310 and 320 and welded in place, further securing fasteners 312 in place in addition to the threading of apertures 320. Structural components 300 may be closed by welding a steel cap on each end, or by another suitable method known in the art.

Figure 12:
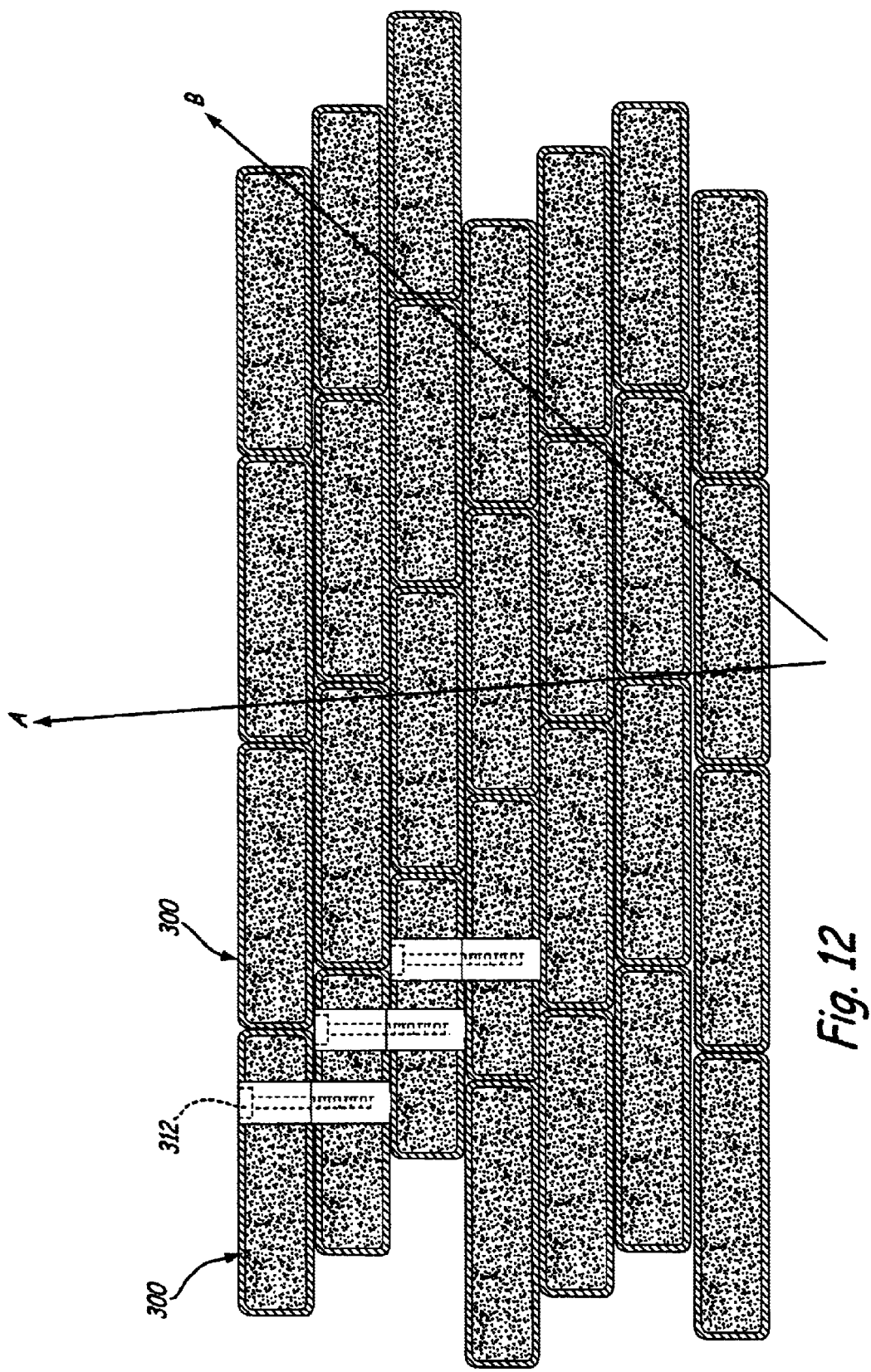
FIG. 12 is a diagram of a shield structure constructed from a plurality of horizontally offset stacked shield component pieces according to an embodiment of the present invention.

Structural components 300*a* and 300*b* shown in FIGS. 8 and 10 are illustrated with apertures 310 and 320 located so that structural components 300*a* and 300*b* interconnect in a fully aligned fashion. In an exemplary embodiment of the present invention, apertures 310 and 320 are offset in such a manner that structural components 300*a* and 300*b* are stacked with a horizontal offset from one another. FIG. 12 is a diagram illustrating a horizontally offset shielding stack according to an embodiment of the present invention. Structural components 300 are horizontally offset from one another in adjacent vertical layers, so that the seams between structural components 300 are not vertically aligned. Lines A and B shown in FIG. 12 illustrate two paths for radiation to travel through the offset shielding structure. The vertical path shown by line A travels through a relatively small number of seams between structural components 300, due to the horizontal offset of adjacent layers of those components. The diagonal path shown by line B travels through a larger number of seams between structural components, which would have a tendency to attenuate the radiation less, since the seams are composed of a structural material such as steel or stainless steel that attenuates radiation less than the shielding material (such as lead) contained therein. However, since the path of line B with high numbers of aligned seams is diagonal, the radiation must pass through a greater thickness of shielding material than it would for a vertical path, since the radiation passes through the shielding material at an angle rather than vertically. This arrangement of structural components 300 therefore minimizes the required total thickness of the shielding structure.

Figure 13:
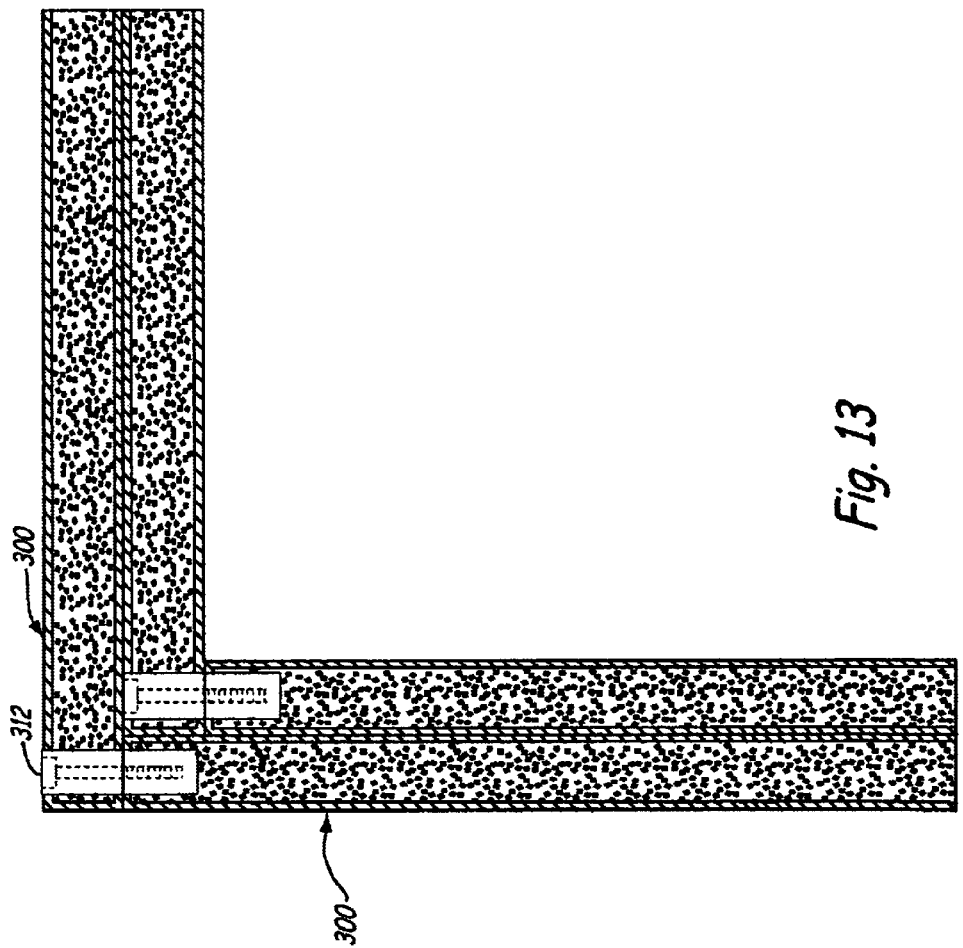
FIG. 13 is a diagram illustrating the general configuration of a border portion of the shielding structure according to an embodiment of the present invention.

An entire shielding structure may be realized by interconnecting a plurality of structural components in the manner shown in FIG. 12. The side borders of the shielding structure are realized in a similar manner, with the end components flipped to a vertical orientation. FIG. 13 is a diagram illustrating the general configuration of a border portion of the shielding structure. Structural components 300 are arranged so that horizontal and vertical components abut one another, and are interconnected by fasteners 312, similar to the interconnection shown in FIG. 12. Based on the exemplary portions of the shielding structure shown in FIGS. 12 and 13, it is within the expertise of one skilled in the art to construct the entire shielding structure of the present invention. Moreover, a number of modifications to the size, shape and/or arrangement of structural components 300 may be made within the scope and spirit of the shielding configuration of the present invention.

The present invention provides an irradiation system with a compact shielding structure for containing radiation within the system to ensure the safety of operating personnel. The irradiation system employs elevators to effect a 90 degree turn/change in elevation that permits the shielding structure to contain radiation by eliminating any straight line paths for radiation to escape from the system. An exemplary embodiment of the shielding structure is modularly constructed with a plurality of appropriately arranged structural components designed for both mechanical strength and shielding capability.

Although the present invention has been described with reference to preferred embodiments, workers skilled in the art will recognize that changes may be made in form and detail without departing from the spirit and scope of the invention.

What is claimed is:

1. An irradiation system comprising:
   a radiation source providing radiation in a localized radiation exposure area;
   a shielding structure around the radiation source, the shielding structure being constructed from a plurality of interconnected structural components each comprising:
      a tubular outer material layer defining an inner chamber therein; and
      a shielding material in the inner chamber; and
   a conveyance system for transporting product into the shielding structure, through the radiation exposure area and out of the shielding structure, the conveyance system comprising:
      an input portion for carrying the product into the shielding structure at a first elevation;
      a first elevator for moving the product from the first elevation to a second elevation different from the first elevation;
      a processing portion for carrying the product at the second elevation through the radiation exposure area;
      a second elevator for moving the product from the second elevation to a third elevation different from the second elevation; and
      an output portion for carrying the product out of the shielding structure at the third elevation.

2. The irradiation system of claim 1, wherein the first elevation is the same as the third elevation.

3. The irradiation system of claim 1, wherein the shielding structure has a floor area of no greater than about 264 square feet.

4. The irradiation system of claim 1, wherein the tubular outer material layer of the interconnected structural components of the shielding structure is composed of steel.

5. The irradiation system of claim 1, wherein the shielding material of the interconnected structural components of the shielding structure is composed of lead.

6. The irradiation system of claim 1, wherein the plurality of interconnected structural components includes a plurality of vertical layers, and wherein structural components in adjacent vertical layers are horizontally offset from one another.

7. The irradiation system of claim 1, wherein the plurality of structural components are interconnected by fasteners extending through at least a portion of adjacent structural components.

8. The irradiation system of claim 1, wherein each of the plurality of structural components has an intrinsic strength sufficient to support its own weight and the weight of an adjacent structural component.

9. An irradiation system comprising:
   a radiation source providing radiation in a localized radiation exposure area;
   a shielding structure around the radiation source; and
   a conveyance system transporting product into the shielding structure, through the radiation exposure area and out of the shielding structure, the conveyance system comprising:
      a first input portion for carrying the product into the shielding structure at a first elevation;
      a second input portion for carrying the product into the shielding structure at the first elevation;
      a first elevator for moving the product from the first input portion at the first elevation to a second elevation different from the first elevation;
      a second elevator for moving the product from the second input portion at the first elevation to the second elevation;
      a first transfer portion for controllably receiving the product from the first and second elevators at the second elevation;

a processing portion for carrying the product from the first transfer portion at the second elevation through the radiation exposure area;

a second transfer portion for receiving the product from the processing portion and controllably passing the product on at the second elevation;

a third elevator for moving the product controllably passed from the second transfer portion at the second elevation to a third elevation different from the second elevation;

a fourth elevator for moving the product controllably passed from the second transfer portion at the second elevation to the third elevation;

a first output portion for carrying the product from the third elevator out of the shielding structure at the third elevation; and a second output portion for carrying the product from the fourth elevator out of the shielding structure at the third elevation.

10. The irradiation system of claim 9, wherein the first elevation is the same as the third elevation.

11. The irradiation system of claim 9, wherein the shielding structure has a floor area of no greater than about 494 square feet.

12. The irradiation system of claim 9, wherein the shielding structure is constructed from a plurality of interconnected structural components each comprising:

a tubular outer material layer defining an inner chamber therein; and a shielding material in the inner chamber.

13. The irradiation system of claim 12, wherein the tubular outer material layer is composed of steel.

14. The irradiation system of claim 12, wherein the shielding material is composed of lead.

15. The irradiation system of claim 12, wherein the plurality of interconnected structural components includes a plurality of vertical layers, and wherein structural components in adjacent vertical layers are horizontally offset from one another.

16. The irradiation system of claim 12, wherein the plurality of structural components are interconnected by fasteners extending through at least a portion of adjacent structural components.

17. The irradiation system of claim 12, wherein each of the plurality of structural components has an intrinsic strength sufficient to support its own weight and the weight of an adjacent structural component.

18. A shielding structure for at least partially surrounding a radiation-generating portion of an irradiation system, the shielding structure comprising:

a plurality of horizontally oriented structural components interconnected with one another; and a plurality of vertically oriented structural components interconnected with one another and with the plurality of horizontally oriented structural components, wherein each of the horizontally oriented structural components and each of the vertically oriented structural components comprise:

a tubular outer material layer defining an inner chamber therein; and a shielding material in the inner chamber.

19. The shielding structure of claim 18, wherein the tubular outer material layer of each of the horizontally oriented structural components and each of the vertically oriented structural components is composed of steel.

20. The shielding structure of claim 18, wherein the shielding material of each of the horizontally oriented structural components and each of the vertically oriented structural components is composed of lead.

21. The shielding structure of claim 18, wherein the plurality of horizontally oriented structural components includes a plurality of vertical layers, and wherein the horizontally oriented structural components in adjacent vertical layers are horizontally offset from one another.

22. The shielding structure of claim 18, wherein the plurality of horizontally oriented structural components and vertically oriented structural components are interconnected by fasteners extending through at least a portion of adjacent structural components.

23. The shielding structure of claim 18, wherein each of the plurality of horizontally oriented structural components and vertically oriented structural components has an intrinsic strength sufficient to support its own weight and the weight of an adjacent structural component.

* * * * *